United States Patent [19]

Pellar

[11] 4,006,094

[45] Feb. 1, 1977

[54] HAND DRYING AND CONDITIONING MATERIAL

[76] Inventor: Marshall Pellar, 7070 Fairway Road, La Jolla, Calif. 92037

[22] Filed: Nov. 7, 1973

[21] Appl. No.: 413,667

[52] U.S. Cl. .............................. 252/194; 252/427; 252/437
[51] Int. Cl.² ......................................... C09K 3/14
[58] Field of Search ............... 252/194, 259.5, 427, 252/437; 106/177; 423/311, 312

[56] References Cited

UNITED STATES PATENTS 1,798,862  3/1931  Baker ................................ 252/194

FOREIGN PATENTS OR APPLICATIONS 510,679  2/1953  Canada ............................ 423/311
223,495  10/1924  United Kingdom ............... 252/194

*Primary Examiner*—Samuel W. Engle
*Assistant Examiner*—Ralph Palo
*Attorney, Agent, or Firm*—Brown & Martin

[57] ABSTRACT

A material comprising wood particles having 1/32 inch screen size or smaller, mixed with a desiccant forming a part by weight of about 2% to 20% of the wood particles, which desiccant is preferably tricalcium phosphate and the wood material is of redwood or peanut hulls or corn husks.

2 Claims, No Drawings

HAND DRYING AND CONDITIONING MATERIAL

BACKGROUND OF THE INVENTION

There are several types of powdered materials that are supposed to improve a person's grip of a racket, bat or the like in sports, or in gripping other articles in related physical activities. Players gripping baseball bats or tennis rackets often experience a slippage or lessening of control of the bat or racket in the players' hands due to perspiration, oils and the like on the hands and on the handle of the racket or bat. Baseball players, for example, employ all types of substances that extend from loose dry dirt gathered by the batter from the ground around home plate to powdered resin and other plastic materials. Usually the material used is intended to increase the player's ability to grip the racket or bat without slippage. Such materials are the powdered resins and plastic materials. However such powdered resins or plastics, while they sometimes absorb some water, sweat or the like, primarily attach to the hands and handle coverings forming sticky surfaces. These sticky surfaces have many disadvantages, only one of which is that it makes it difficult to adjust the handle of the racket or bat in the players' hands. Further, these products in adhering to the hands and handle grips, build-up a sticky residue that remains on the surfaces. So while the batter or tennis player may desire to increase his grip control, he also desires hand surface conditioning, rather than just a sticky surface. Other uses of such materials are by football players, bowlers, javelin throwers, pole vaulters, and many other persons.

It is therefore an advantage to have a new and improved hand drying and conditioning material, that drys and conditions the hands as well as removes perspiration, oils, and the like from the hands as well as from the handle grip of the racket, baseball bat or the like, that improves the grip but does not leave a sticky residue on the hands or on the handle grips.

SUMMARY OF THE INVENTION

In an embodiment of the process and article of this invention, a wood material having a small particle size is mixed as a base with a small portion of a desiccant material. The desiccant material comprises about a 2% to 20% by weight of the wood material and preferably is tri-calcium phosphate. The wood material, as used and designated herein, includes ground particles of redwood or peanut hulls or corn husks. These materials may be used individually or in combination. Also preferably the wood material is ground to a 1/32 inch screen size or smaller.

The hand drying and conditioning material of the invention, is applied directly to the hands and handle of the article, be it a tennis racket handle or the handle of a ball bat or the like, and the material is rubbed against the hands and handle. The material absorbs water, perspiration, skin oils and the like in this rubbing process and because of the roughness or coarseness of the wood particles, the material falls off of the hands and the handle removing the aforesaid perspiration, oils and the like in the process. Further the desiccant aids in removing the perspiration, oils and the like, and also leaves a small portion or thin layer of desiccant on the hands and also on the handle grip surface. The particles of wood including the hulls effectively remove such perspiration and oils from the leather grips, such as are on baseball bat handles, tennis racket handles, and the like.

The application of the materials of this invention does not make the hands sticky, as the material does not stick to the hands and handle grip other than the thin layer of desiccant. The particles fall off leaving only the thin surface of desiccant or drying agent. Subsequent applications of the material merely remove the previous layer of desiccant, if any remains, and applies a new layer. Thus the hands are conditioned and in effect cleaned and with a desiccant applied thereto, which improves the normal and natural grip that a person is able to exert onto a racket handle or the like, which grip has the normal and desired amount of natural friction, without being sticky. This not only improves a persons ability to grip and control the racket or bat, but improves the feeling of control that a person experiences in effectively gripping the handle.

It is therefore an object of this invention to provide a new and improved material and process for hand drying and conditioning.

In the practice of this invention, a wood material, which for the purpose of this invention comprises particles of redwood or peanut hulls or corn husks, are ground into particles have a screen size of 1/32 of an inch or smaller. To this is mixed a small quantity of a desiccant material in a quantity of about 2% to 20% by weight of the wood particle base. The desiccant material may be of any suitable desiccant material, however applicant has found that it is particularly advantageous and a part of this invention to employ tri-calcium phosphate as the desiccant material. Applicant has experimented with several different types of wood and hull particles, and has found that the preferred and best particles and the one that forms a part of this invention are particles from redwood or peanut hulls or corn husks, or a combination thereof.

Applicant has found that if the percentage of desiccant is less than 2% it is generally ineffective, and if the desiccant comprises more than 20% by weight of the wood particles, the material has an excessive drying capability.

EXAMPLE 1

Ten pounds of wood particles of redwood, ground to 1/32 of an inch screen size or smaller and were mixed with 20% by weight of tri-calcium phosphate. The resultant mixture was used repeatedly by user on his hands and found to condition the hands and remove perspiration and oils therefrom while playing baseball.

EXAMPLE 3

Three pounds of corn husks were ground into a size of 1/32 of an inch screen size or smaller, and mixed with 15% by weight of tri-calcium phosphate and repeatedly used on a users hands who was bowling and found to condition the users hands and remove perspiration and oil therefrom.

Having disclosed my invention, I now claim:

1. A hand drying and conditioning material comprising in combination:
    a base of wood material in small rough particles having a particle size of 1/32" screen size or smaller,
    a small quantity of powdered tricalcium phosphate desiccant material comprising two to twenty percent by weight of said wood particles, said wood particles being selected from the group consisting of redwood, peanut hulls, and corn husks.

2. The process of providing a hand drying and conditioning material which comprises:

grinding a wood material to rough particles having a particle size of 1/32" screen size or smaller, mixing a powdered tricalcium phosphate desiccant material in said wood particles to comprise two to twenty percent by weight of said wood material, said wood material being selected from the group consisting of redwood, peanut hulls and corn husks.

* * * * *